(12) United States Patent
Falahee

(10) Patent No.: US 7,608,094 B2
(45) Date of Patent: Oct. 27, 2009

(54) PERCUTANEOUS FACET FIXATION SYSTEM

(75) Inventor: Mark H. Falahee, Ann Arbor, MI (US)

(73) Assignee: U.S. Spinal Technologies, LLC, Boca Raton, FL (US)

( * ) Notice: Subject to any disclaimer, the term of this patent is extended or adjusted under 35 U.S.C. 154(b) by 505 days.

(21) Appl. No.: 10/683,076

(22) Filed: Oct. 10, 2003

(65) Prior Publication Data
US 2004/0143268 A1 Jul. 22, 2004

Related U.S. Application Data

(60) Provisional application No. 60/417,543, filed on Oct. 10, 2002.

(51) Int. Cl.
*A61B 17/70* (2006.01)

(52) U.S. Cl. .................................................. 606/247
(58) Field of Classification Search ................. 606/61, 606/73
See application file for complete search history.

(56) References Cited

U.S. PATENT DOCUMENTS 6,669,698 B1   12/2003   Tromanhauser et al. ....... 606/61

*Primary Examiner*—Anu Ramana
(74) *Attorney, Agent, or Firm*—Gifford, Krass, Sprinkle, Anderson & Citkowski, P.C.

(57) ABSTRACT

A percutaneous facet fixation system minimally invasive, reproducible, efficient, and effective. Capable of immediate stabilization of a facet joint complex, the instrumentation and methods may be used with C-arm and/or endoscopic visualization.

25 Claims, 3 Drawing Sheets

PERCUTANEOUS FACET FIXATION SYSTEM

REFERENCE TO RELATED APPLICATION

This application claims priority from U.S. Provisional Patent Application Ser. No. 60/417,543, filed Oct. 10, 2002, the entire content of which is incorporated herein by reference.

FIELD OF THE INVENTION

This invention relates generally to spine surgery and, in particular, to a percutaneous facet fixation system.

BACKGROUND OF THE INVENTION

For patients with a high degree of spinal instability (e.g. fractures), or in revision surgery, a combination anterior/posterior fusion is indicated at one or more levels. Fusing both the front and back provides a high degree of stability for the spine and a large surface area for the bone fusion to occur. The disc may be approached either as an anterior lumbar interbody fusion (ALIF), or as a posterior lumbar interbody fusion (PLIF). Both procedures are well known to those of skill in the art.

To further stabilize vertebral segments, posterior instrumentation is often performed in conjunction with an interbody fusion. The most commonly used posterior instrumentation system in use today is pedicle screw fixation. The major disadvantage to this technique is the necessity of major muscle dissection, which can lead to morbidity and scarring.

Facet screw fixation offers the advantage of placing a single screw across each articulating facet joint to immobilize a motion segment, thereby reducing the amount of hardware (and therefore exposure) necessary. Existing techniques, however, still demand relatively open procedures, such that the need remains for a facet fixation system compatible with minimally invasive surgical (MIS) procedures.

SUMMARY OF THE INVENTION

The present invention is a percutaneous system of facet fixation that is minimally invasive, reproducible, efficient, and effective. Capable of immediate stabilization of a facet joint complex, the instrumentation and methods may be used with C-arm and/or endoscopic visualization.

DETAILED DESCRIPTION OF THE INVENTION

Figure 1:
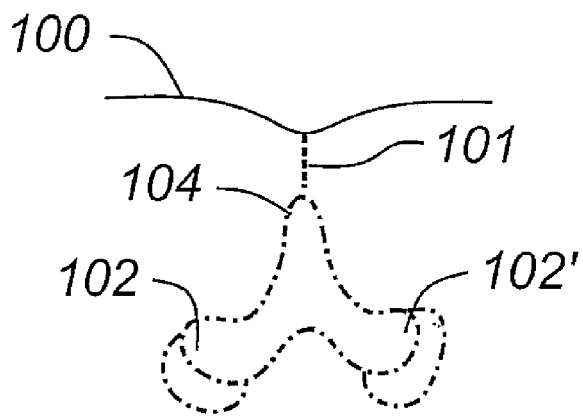
FIG. 1 is a highly-simplified drawing that shows the facet joints of a patient to which this invention is applicable.

Reference is now made to the drawings, wherein FIG. 1 is a highly-simplified drawing that shows the facet joints 102, 102' of a patient 100 to which this invention is applicable. The proximal spinous process is indicated at 104. The patient is placed in a prone position under general anesthetic. A C-arm is preferably utilized to determine fixation level and approach for incision.

Figure 2:
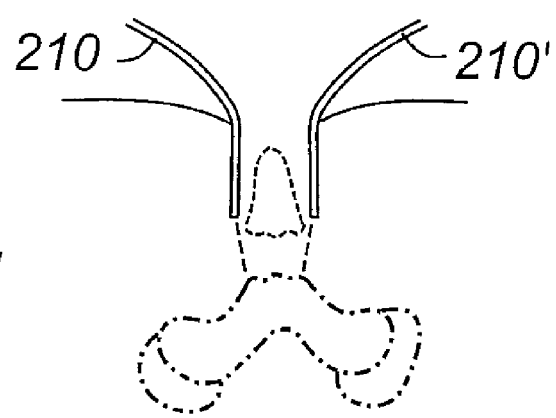
FIG. 2 is a drawing showing a posterior approach to the spine using retractors and removal of the spinous process to the junction to the lamina.

A 1.0-inch incision 101 (or thereabouts) is made in midline over the proximal spinous process 104. (For L4-L5 fixation, the incision made over L4 spinous process.) As shown in FIG. 2, the spinous process removed to junction of lamina, allowing access angle to facet joints bilaterally.

Figure 3:
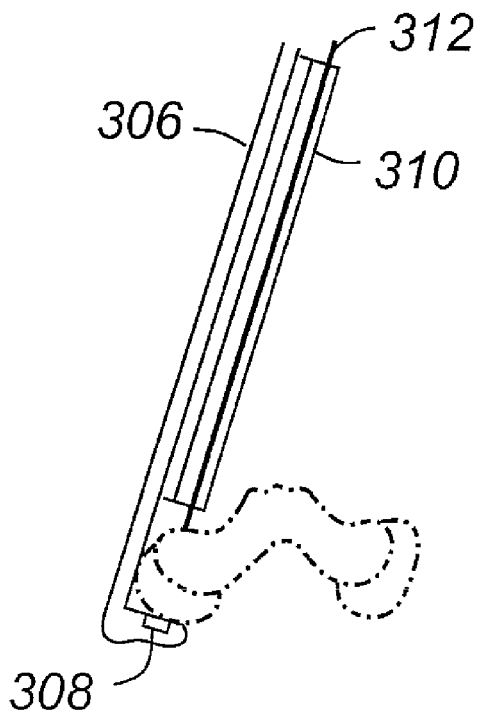
FIG. 3 is a drawing that shows a guide wire passed by C-arm or endoscopic guidance to a facet joint in conjunction with the lower arm of the facet gun.

FIG. 3 is a drawing that shows the way in which a guide wire 312 is passed by C-arm or endoscopic guidance to a facet joint in conjunction with the lower arm of a facet gun 306 according to the invention. The lower arm of facet gun contains a deep locking nut 308 abutting lateral surface of the superior facet (L5). The deep locking nut is positioned in alignment with the guide wire 312 by C-arm past the facet joint.

Figure 4:
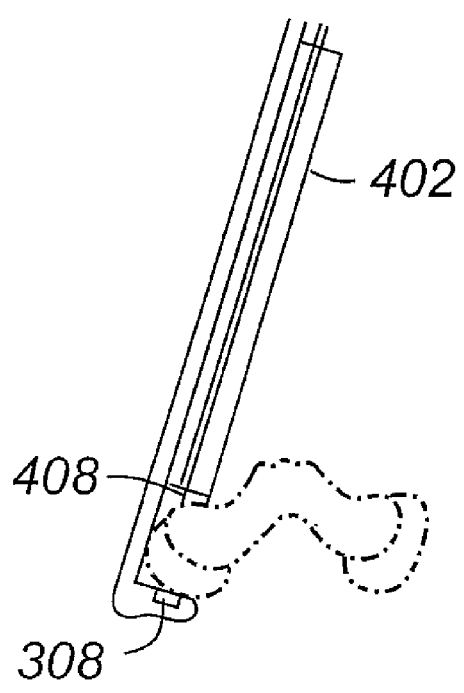
FIG. 4 is a drawing that shows the upper arm of the facet gun, including a locking nut, inserted along the track of the guide wire of FIG. 3.
Figure 5:
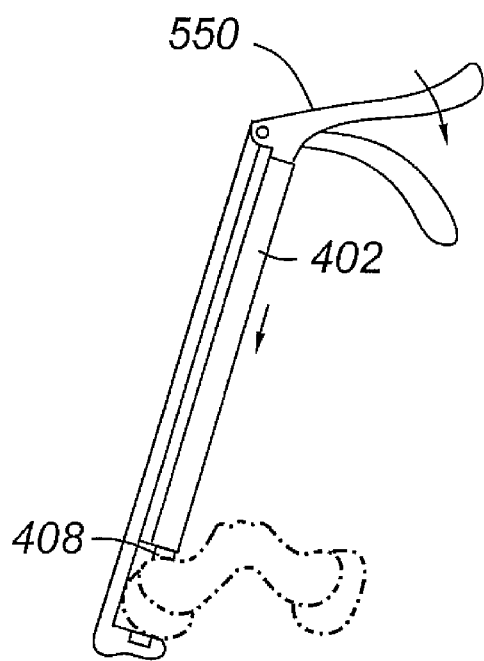
FIG. 5 shows the handle of a facet gun compressed, locking the nuts onto the upper and lower surfaces of the facet joint.

FIG. 4 is a drawing that shows the upper arm of the facet gun 310, including a locking nut 408, also inserted along the track of the guide wire of FIG. 3. The superficial locking nut 408 is inserted over the guide sleeve of lower arm, making contact with surface of inferior facet. As shown in FIG. 5, the handle of the facet gun compressed, holding the nuts 408, 308 onto upper and under surface of facet joint.

Figure 6:
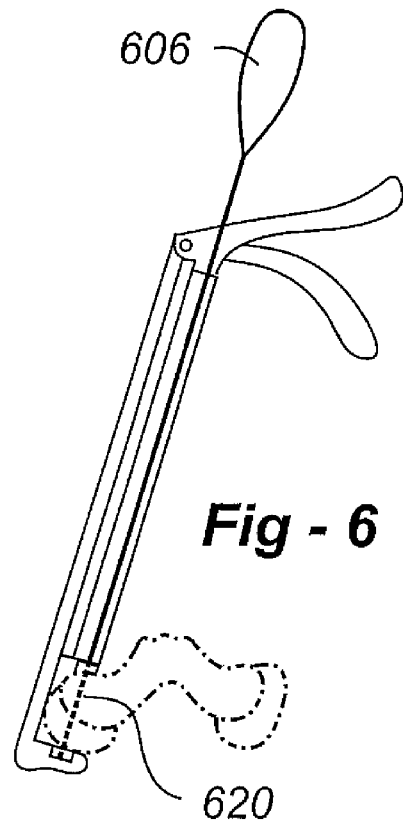
FIG. 6 shows how a bolt is driven through the superficial and deep nuts, thereby fusing the facet joint.
Figure 12:
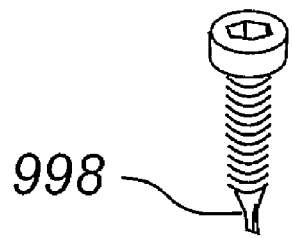
FIG. 12 is a drawing of a bolt including a drill bit tab useful to the invention.

Referring to FIG. 6, a previously selected facet bolt, preferably with drill bit head 998 as shown in FIG. 12, is inserted into barrel of upper facet gun sleeve. The bolt is driven through superficial and deep nuts using a manually operated tool 606, passing through facet joint, locking into the superficial nut and compressing the joint together.

Figure 7:
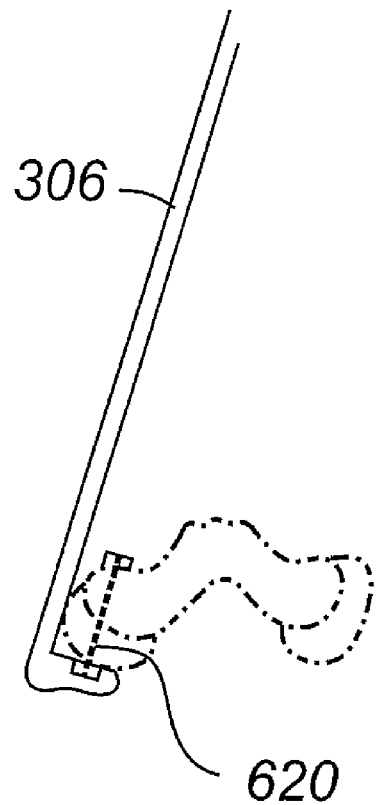
FIG. 7 shows the fused joint with the lower arm of the facet gun still in position.
Figure 8:
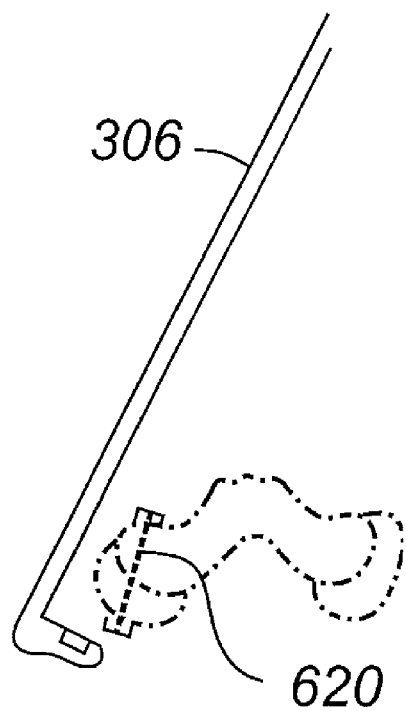
FIG. 8 shows the removal of the lower arm.

The upper arm of facet gun is disengaged in FIG. 7. The lower arm is pushed deeper, disengaging itself from the deep nut, and the arm and guide wire are removed as shown in FIG. 8. The procedure is then repeated for opposite side.

Figure 9:
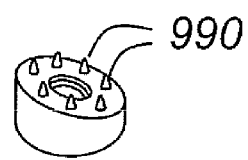
FIG. 9 shows an alternative embodiment of a nut applicable to the invention, including fixation spikes.
Figure 10:
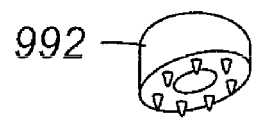
FIG. 10 shows the use of a washer according to the invention, which may be wedge-shaped and which may use fixation spikes.
Figure 11:
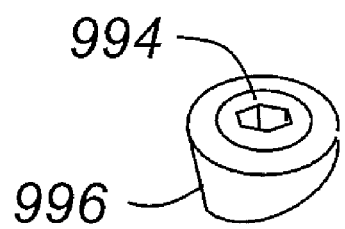
FIG. 11 is a drawing that shows the way in which a bolt head seats inside of a top nut through a click lock.

FIG. 9 is a drawing that shows an alternative nut useful in conjunction with the invention, including an optional wedge-shape and, independent of that, the use of fixation spikes 990 operative to dig into the bone, particularly during and after compression of the joint. FIG. 10 shows how the upper nut, in particular, may be replaced with a washer 992 devoid of threats. Optionally, as with the lower locking nut, the shape of the washer in FIG. 10 may be wedge-shaped or contoured to match the facet surface, and may include optional fixation spikes as well. FIG. 11 shows the way in which a bolt head 994 may seat inside of the top nut 996, and locking in position with click stops (not visible in the picture).

I claim:

1. A method of fusing a facet joint, comprising the steps of:
   providing a deep locking nut and a physically separate facet bolt;
   positioning the deep locking nut so as to abut the lateral surface of a superior facet forming part of a facet joint;

driving the facet bolt through the facet joint and the deep locking nut, thereby compressing the facet joint.

2. The method of claim 1, further including the step of:
providing instrumentation configured to hold the deep locking nut in position while driving the facet bolt; and
disengaging and removing the instrumentation once the facet joint is compressed.

3. The method of claim 2, wherein the deep locking nut is wedge-shaped.

4. The method of claim 2, wherein the instrumentation including a pair of elongate members, one with a bent distal end to hold the deep locking nut.

5. The method of claim 2, further including the step of making a midline incision over the proximal spinous process to access the facet joint with the instrumentation.

6. The method of claim 1, wherein the deep locking nut includes a plurality of fixation spikes.

7. The method of claim 1, further including the steps of:
providing an unthreaded washer for contacting an inferior facet; and
driving the facet bolt through the washer before the facet bolt engages with the deep locking nut.

8. The method of claim 7, wherein the washer includes a plurality of fixation spikes.

9. The method of claim 7, wherein the washer is wedge-shaped.

10. The method of claim 1, further including the step of compressing the facet joint prior to the step of driving the facet bolt.

11. The method of claim 1, wherein the step of providing a facet bolt includes the provision of a self-drilling facet bolt.

12. The method of claim 1, further including the step of locking the facet bolt and the deep locking nut.

13. A method of fusing a facet joint, comprising the steps of:
providing a deep locking nut and a physically separate facet bolt;
providing instrumentation including a bent distal end to hold the deep locking nut and drive the facet bolt through facet joint and the deep locking nut;
positioning the bent distal end of the instrumentation behind the facet joint such that the deep locking nut abuts the lateral surface of a superior facet forming the facet joint;
operating the instrumentation to drive the facet bolt through the facet joint until the bolt locks with the deep locking nut;
disengaging the holder on the bent distal end of the instrumentation from the deep locking nut; and
removing the instrumentation.

14. The method of claim 13, wherein the deep locking nut includes a plurality of fixation spikes.

15. The method of claim 13, wherein the deep locking nut is wedge-shaped.

16. The method of claim 13, further including the steps of:
providing an unthreaded washer for contacting an inferior facet; and
driving the facet bolt through the washer before the facet bolt engages with the deep locking nut.

17. The method of claim 16, wherein the washer includes a plurality of fixation spikes.

18. The method of claim 16, wherein the washer is wedge-shaped.

19. The method of claim 13, wherein the instrumentation includes a user control operative to compress the facet joint prior to driving the facet bolt.

20. The method of claim 13, further including the step of locking the facet bolt and the deep locking nut.

21. A method of fusing a facet joint, comprising the steps of:
providing a deep locking nut, a facet bolt, and an unthreaded washer;
providing instrumentation including a bent distal end with a holder for the deep locking nut, a handle for compressing a facet joint, and a tool for driving the facet bolt through the washer and into deep locking nut;
positioning the bent distal end of the instrumentation such that the deep locking nut abuts the lateral surface of a superior facet forming the facet joint;
positioning the washer so as to contact an inferior facet forming the facet joint;
operating the handle so as to compress the washer and deep locking nut, thereby compressing the facet joint;
operating the tool to drive the facet bolt through the washer and facet joint until locking with the deep locking nut; and
disengaging the holder on the bent distal end of the instrumentation from the deep locking nut and removing the instrumentation.

22. The method of claim 21, wherein the deep locking nut includes a plurality of fixation spikes.

23. The method of claim 21, wherein the deep locking nut is wedge-shaped.

24. The method of claim 21, wherein the washer includes a plurality of fixation spikes.

25. The method of claim 21, wherein the washer is wedge-shaped.

* * * * *

UNITED STATES PATENT AND TRADEMARK OFFICE
CERTIFICATE OF CORRECTION

PATENT NO. : 7,608,094 B2  Page 1 of 1
APPLICATION NO. : 10/683076
DATED : October 27, 2009
INVENTOR(S) : Mark Falahee It is certified that error appears in the above-identified patent and that said Letters Patent is hereby corrected as shown below:

Please insert (56) References Cited
The following references that were submitted in Information Disclosure Statements, but were omitted from the cover of the patent:

| | | |
|---|---|---|
| --5,527,312 | 6/1996 | Ray |
| 5,558,674 | 9/1996 | Heggeness et al. |
| 6,485,518 | 11/2002 | Cornwall et al. |
| 6,540,747 | 4/2003 | Marino |
| 6,648,893 | 11/2003 | Dudasik |
| 6,811,567 | 11/2004 | Reiley |
| 6,949,123 | 9/2005 | Reiley |
| 6,966,930 | 11/2005 | Amin et al. |
| 7,041,136 | 5/2006 | Goble et al. |
| 7,060,068 | 6/2006 | Tromanhauser et al. |
| 2004/0111093 | 6/2004 | Chappuis |
| 2004/0225360 | 11/2004 | Malone |
| 2004/0254575 | 12/2004 | Obenchain et al. |
| 2005/0124993 | 6/2005 | Chappuis |
| 2005/0149030 | 4/2005 | Serhan et al. |
| 2005/0273110 | 12/2005 | Boehm, Jr. et al. |
| 2006/0004367 | 1/2006 | Alamin et al. |
| 2006/0111779 | 5/2006 | Petersen |
| 2006/0111780 | 5/2006 | Petersen-- |

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

PATENT NO.        : 7,608,094 B2                                              Page 1 of 1
APPLICATION NO. : 10/683076
DATED             : October 27, 2009
INVENTOR(S)       : Mark H. Falahee It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1071 days.

Signed and Sealed this

Twelfth Day of October, 2010

David J. Kappos
*Director of the United States Patent and Trademark Office*